United States Patent
Makhija et al.

(10) Patent No.: US 11,266,848 B2
(45) Date of Patent: Mar. 8, 2022

(54) SYSTEM, METHOD AND DEVICE FOR NEURAL ACTIVITY CONTROL

(71) Applicants: Tara Makhija, Westfield, NJ (US); Abhishek Mhatre, Summit, NJ (US); Chi Kin Nathan Lam, Westfield, NJ (US)

(72) Inventors: Tara Makhija, Westfield, NJ (US); Abhishek Mhatre, Summit, NJ (US); Chi Kin Nathan Lam, Westfield, NJ (US)

( * ) Notice: Subject to any disclaimer, the term of this patent is extended or adjusted under 35 U.S.C. 154(b) by 248 days.

(21) Appl. No.: 16/595,519

(22) Filed: Oct. 8, 2019

(65) Prior Publication Data
US 2021/0101014 A1    Apr. 8, 2021

(51) Int. Cl.
*A61N 1/40*    (2006.01)
*A61N 1/36*    (2006.01)
*A61N 1/18*    (2006.01)

(52) U.S. Cl.
CPC ..................................... *A61N 1/40* (2013.01)

(58) Field of Classification Search
CPC .................................................. A61N 1/36025
See application file for complete search history.

(56) References Cited

U.S. PATENT DOCUMENTS

| | | | |
|---|---|---|---|
| 2006/0145302 A1* | 7/2006 | Kim ......................... | C09D 5/32 257/629 |
| 2014/0330353 A1* | 11/2014 | Knight ................. | A61N 1/0529 607/101 |
| 2017/0216594 A1* | 8/2017 | Grossman .............. | A61N 1/323 |
| 2019/0046794 A1* | 2/2019 | Goodall ............... | A61N 1/0456 |
| 2019/0366088 A1* | 12/2019 | Wang ................. | A61N 1/36025 |

OTHER PUBLICATIONS

Grossman et al.; "Noninvasive Deep Brain Stimulation via Temporally Interfering Electric Fields;" Cell 169; 1029-1041; Published by Elsevier Inc.; Published Jun. 1, 2017. (Year: 2017).*

\* cited by examiner

*Primary Examiner* — Daniel J Colilla

(57) ABSTRACT

The present invention provides a wearable device, a system for manufacturing a wearable device and a method of neural activity control. The device for temporal interference simulation includes a pair of electrodes at penalizable location. The electrodes each send out a high frequency electromagnetic fields with a very slight difference in the two frequencies. The fields superimpose at a specified region of the brain, which is customized depending on the location of neural activity control, to create a low frequency refractory wave envelope. The low frequency wave inhibits or stimulates local neurons to control electrical activity within that region.

12 Claims, 5 Drawing Sheets

SYSTEM, METHOD AND DEVICE FOR NEURAL ACTIVITY CONTROL

BACKGROUND

1. Technical Field

The present invention generally relates to electrical-medical impulses for neurological conditions of a subject. More particularly, the invention relates to system, device and method for neural activity control in a subject.

2. Description of the Prior Art

Neuroscience is the scientific field pursuing the understanding of the nervous system, its structure, and function. The brain is known to be comprised of neural pathways that are connected to send or receive signals. These signals are delivered in the form of electrochemical impulses that allow communication throughout the nervous system. Once a signal is transmitted, it elicits some response, generally either creating some form of movement in the body or allowing the receival of sensory input. However, neural complications arise when the electrochemical impulses become erratic, which occurs in patients with Parkinson's Disease, epilepsy, or other neurological conditions. As the impulses are sent irregularly, they elicit irregular responses, which could lead to a variety of disorders depending on the affected region of the brain.

A surgical procedure exists in order to regulate irregular neural activity caused by the erratic electrochemical impulses, however this procedure can only help regulate activity based in the basal ganglia region of the brain, which controls movement. This surgery is known as Deep Brain Stimulation (DBS), and involves drilling an electrode into the brain. The electrode sends out electrical impulses to the basal ganglia, which help regulate electrochemical impulses sent through neural networks in the brain. The electrode works similarly to a pacemaker by sending out impulses at regular intervals to keep erratic activity in sync. Deep Brain Stimulation is used on the basal ganglia only as the electrode cannot be implanted into other regions of the brain without affecting the rest of the brain. In other words, the surgical nature of the procedure inhibits its ability to be used as on effective treatment for any neurological condition, and it is used only to treat movement-based disorders.

In recent years, a non-invasive process that has yielded promising results have been developed for treating the neurological conditions. One prior art US20180345006A1 provides electrode apparatus for non-invasively applying electrical stimulation to a body portion of a human subject by way of a skin interface. The device uses many electrodes at many points on the skull. The Electrodes are connected using electrolyte skin connection and are all electrically coupled to each other. The device is constructed in a conical manner and includes extensive amount of hardware. However, such processes lack precise determination of location in the brain to be treated, complicated use of device which requires medical supervision and not advisable to be used by the patient on their own, bulky structural configuration with high risk factors involved in using such devices, etc.

Further, the neural activity in a subject may not only be related for treatment of neurological condition but it may be an important aspect for enhancing productivity and focus of a human mind. However, it is extremely difficult to accurately determine the location in a brain that would enable a mind to think more productively if the neurons in that region are subjected to impulses.

In view of the above, there exists a continuing need to provide systems and methods that overcome the shortcoming associated with the prior arts.

SUMMARY OF THE INVENTION

Accordingly, the present invention provides a wearable device for neural activity control in a subject. The device includes at least two pairs of electrodes to be placed spaced apart fem each other and configured for transmitting electromagnetic field signals of different frequencies to be superimposed at a target region of brain of a subject; and a control module connected to the at least two pairs of electrodes for controlling operation of the device, wherein the superimposed field signals generate a low frequency refractory wave envelope at the target region wherein the low frequency refractory wave inhibits or stimulates a plurality of local neurons to control electrical neural activity within the target region in the brain of the subject.

In an embodiment, the present invention provides a method of neural activity control in a subject. The method includes placing a pair of ear pieces of a wearable device on the ears of a subject so that a pair of electrodes placed inside each of the pair of earpieces contacts the subject's skin wherein each of the pair of electrodes is configured for transmitting electromagnetic field signals of different frequencies to be superimposed at a target region of brain of the subject; attaching a control module of the wearable device around the neck of the subject wherein the control module is connected to the pair of ear pieces via a pair of coaxial cables for controlling operation of the device; and driving stimulation between the pair of ear pieces through the superimposed field signals that generate a low frequency refractory wave envelope at the target region wherein the low frequency refractory wave inhibits or stimulates a plurality of local neurons to control electrical neural activity within the target region.

In an embodiment, the present invention provides a system for manufacturing a wearable device configured for neural activity control in a subject. The system includes a computing means configured for analyzing a subject to determine a target region in brain of a subject requiring neural control wherein the computing means analyzes head structure of the subject along with the target region for determining configuration of a pair of ear piece of a wearable device to be manufactured; and a 3D printer configured for receiving a printing command from the computing device to print manufacture the pair of ear piece of the wearable device such that an electrode placed inside each of the pair of ear piece contacts the subject's skin wherein each of the electrodes is configured for transmitting electromagnetic field signals of different frequencies to be superimposed at the target region of brain of the subject to generate a low frequency refractory wave envelope at the target region wherein the low frequency refractory wave inhibits or stimulates a plurality of local neurons to control electrical neural activity within the target region.

In a related embodiment the present invention provides a method for manufacturing a wearable device configured for neural activity control in a subject. The method includes analyzing by a computing device, a subject to determine a target region in brain of the subject that requires neural activity control; determining configuration of a pair of ear piece of a wearable device to be manufactured based on head structure of the subject and the identified target region; and in response to determination or required configuration of the ear piece, issuing a printing command to a 3D printer by the computing device to print manufacture the pair of ear piece of the wearable device such that an electrode placed inside each of the pair of ear piece is able to contact the subject's skin wherein each of the electrodes is configured for transmitting electromagnetic field signals of different frequencies to be superimposed at the target region of brain of the subject to generate a low frequency refractory wave envelope at the target region wherein the low frequency refractory wave inhibits or stimulates a plurality of local neurons to control electrical neural activity within the target region.

In an advantageous aspect the present invention controls neural activity for treating a neurological condition caused by irregular neural activity in the brain of the subject through neural regulation and at the same time the present invention controls neural activity for enhancing memory and cognition of the brain of a subject through neural stimulation at the target region by application of a positive (anodal) or negative (cathodal) current to the target region, facilitating depolarization or hyperpolarization of neurons. The neural stimulation is driven using pulses of direct current to stimulate and increase productivity and focus on the brain.

BRIEF DESCRIPTION OF THE DRAWINGS

The disclosure will be better understood and when consideration is given to the drawings and the detailed description which follows. Such description makes reference to the annexed drawings wherein.

DETAILED DESCRIPTION

Figure 1:
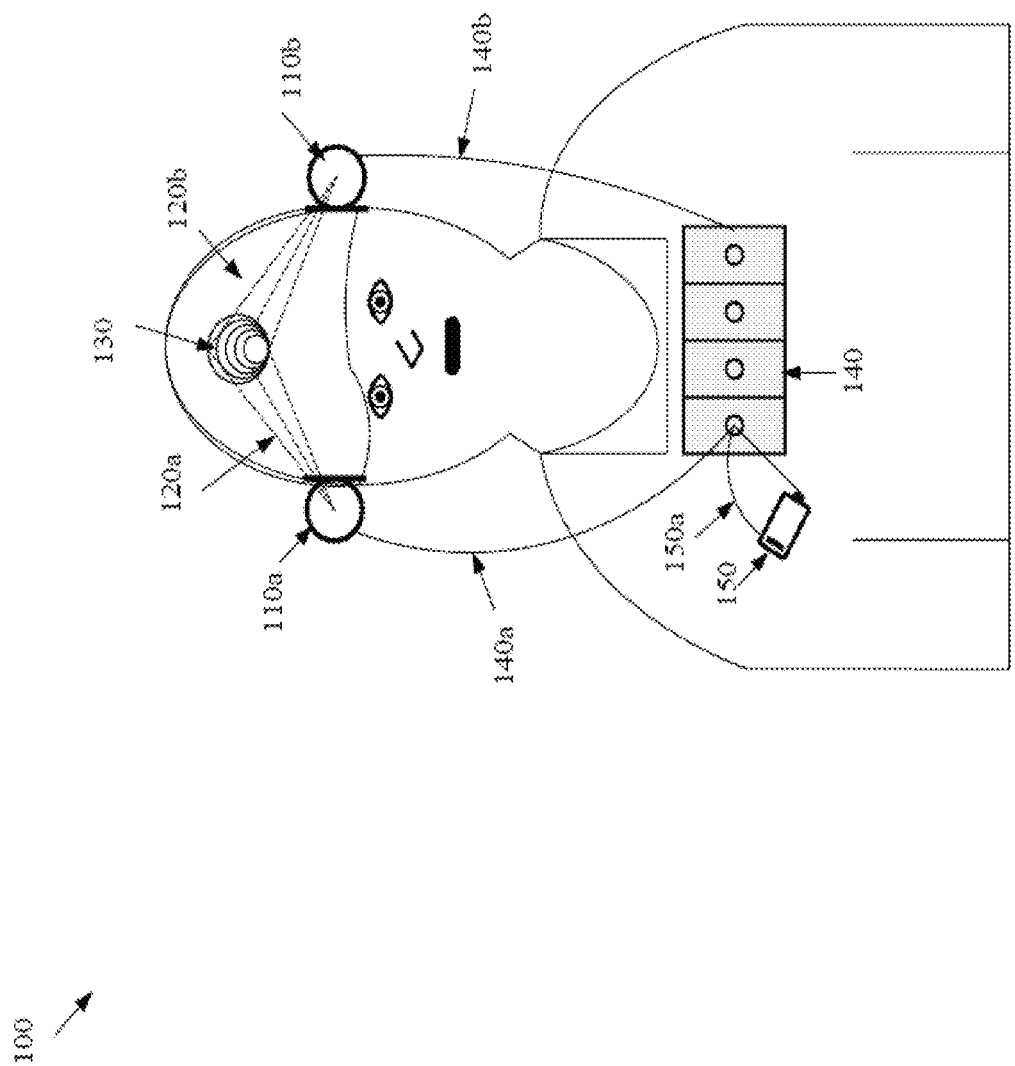
FIG. 1 is a view of a wearable device placed on a subject for neural activity control in accordance with an embodiment of the invention.

Described herein are nonlimiting example embodiments of the present invention, which includes neural regulation in a subject by a wearable device manufactured through a system for controlling neurological activity in a subject.

The various embodiments including the example embodiments will now be described more fully with reference to the accompanying drawings, in which the various embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, the sizes of components may be exaggerated for clarity.

It will be understood that when an element or layer is referred to as being "on," "connected to," or "coupled to" another element or layer, it can be directly on, connected to, or coupled to the other element or layer or intervening elements or layers that may be present. As used herein, the term "and/or" includes any and all combinations of one or more of the associated listed items.

Spatially relative terms, such as "signals," "impulses," or "field," and the like, may be used herein for ease of description to describe one element or feature's relationship to another element(s) or feature(s) as illustrated in the figures. It will be understood that the spatially relative terms are intended to encompass different orientations of the structure in use or operation in addition to the orientation depicted in the figures.

The subject matter of various embodiments, as disclosed herein, is described with specificity to meet statutory requirements. However, the description itself is not intended to limit the scope of this patent. Rather, the inventors have contemplated that the claimed subject matter might also be embodied in other ways, to include different features or combinations of features similar to the ones described in this document, in conjunction with other technologies. Generally, the various embodiments including the example embodiments relate to a wearable device, system and method of neural activity control in a subject.

Figure 1A:
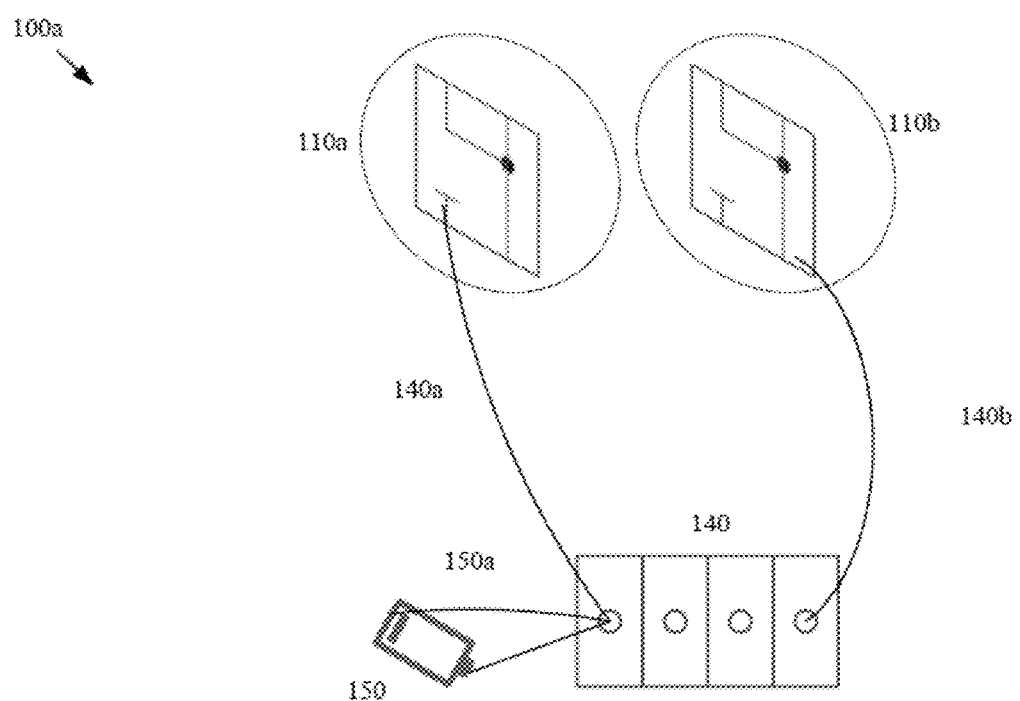
FIG. 1*a* is a perspective view the wearable device for neural activity control in accordance with an embodiment of the invention.

Referring to FIGS. 1 and 1*a*, a perspective view 100 of a wearable device 100*a* placed on a subject for neural activity control is provided in accordance with an embodiment of the present invention. The device 100*a* includes a pair of electrodes 110 (110*a*, 110*b*) generating electromagnetic fields 120 (120*a*, 120*b*) to be superimposed at a target region 130 inside a brain of a subject. The device 100*a* includes a control module 140 connected to the pair of electrodes 110 by a pair of coaxial cables (140*a*, 140*b*). The device 100*a* also includes a power battery 150 connected to the control module 140 by power cable 150*a*.

In an embodiment, the device 100*a* further includes a plurality of variable attenuators for controlling magnitude of the refractory waves and circularly polarized waves to minimize energy loss during wave collisions.

In an embodiment, the pair of electrodes 110 operate at a frequency in the range of 2000 Khz and a difference in frequency between the pair of electrodes is 10 khz.

In an embodiment, the superimposition of the electromagnetic fields 120 at the target region 130 is customizable through an angle and orientation of the pair of electrodes 110. On superimposition the difference in frequency creates the low frequency envelope that regulates the irregular neural activity within the target region 130 of the brain without affecting normally functioning regions of the brain. Also, for neural stimulation the target region 130 is identified to control neural activity for enhanced memory, increased productivity and focus of the brain.

In an exemplary embodiment, the device 100*a* provides each of the electrodes 110 as part of an earpiece to be placed around ears of the subject to ensure snug contact between skin of the subject and the electrodes where the device includes suction, adhesion and hooks to ensure appropriate fit for the subject. Further, the device includes shielding to maintain integrity to prevent unwanted radiation paths. The earpiece is made of ABS plastic and other components so that it does not interfere with electric impulse delivering stimulus to the regions of the brain.

In an embodiment, the device 100*a* includes a circularly polarized patch antenna antenna/electrodes with axial ratio close to 0.8.

In an embodiment, the device 100*a* may enable communication of electrodes 110 with the control module 140 wirelessly through communication interface, which may include signal processing circuitry. Also, the device may be implemented in a number of different forms, for example, as an earpiece, or other similar devices.

The control module 140 includes components such as electric impulse generators, processor, memory, a microcontroller, a frequency regulator, and storage device amongst others. These components are customized for use and structuring as part of the control module as per application and requirement for a subject depending on the neurological condition and the kind of regulation required. The present invention reflects the frequency and pattern of impulse control as per requirement.

The processor may be implemented as a chipset of chips that include separate and multiple analog and digital processors. The processor may provide coordination of the other components, such as controlling user interfaces, applications run by devices, and wireless communication by devices. The Processor may communicate with a user through control interface and display interface coupled to a display. The display may be, for example, a TFT LCD (Thin-Film-Transistor Liquid Crystal Display) or an OLED (Organic Light Emitting Diode) display, or other appropriate display technology. The display interface may comprise appropriate circuitry for driving the display to present graphical and other information to an entity/user. The control interface may receive commands from a user and convert them for submission to the processor. In addition, an external interface may be provided in communication with processor, so as to enable near area communication or device with other devices. External interface may provide, for example, for wired communication in some implementations, or for wireless communication in other implementations, and multiple interfaces may also be used.

Figure 2:
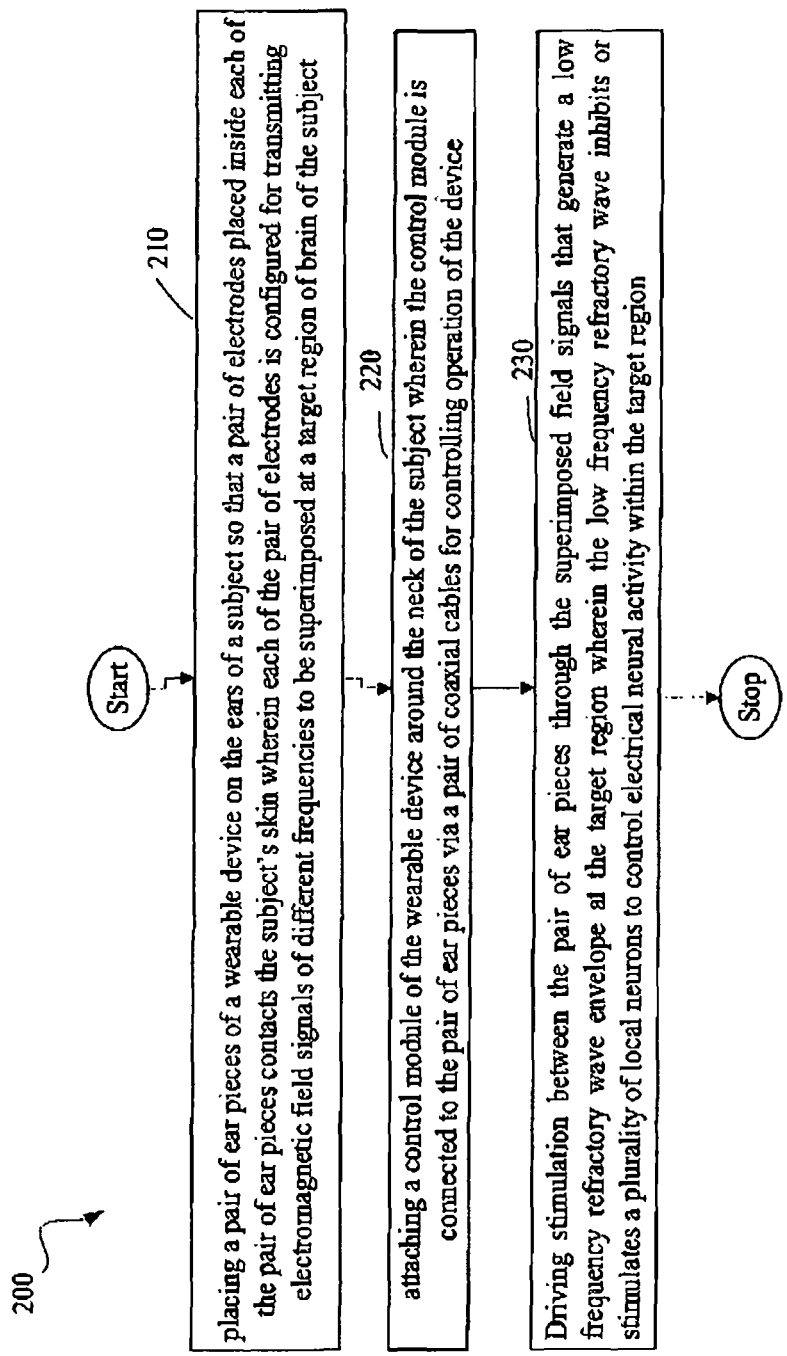
FIG. 2 is a flowchart depicting a method of neural activity control in accordance with an embodiment of the invention.

Referring to FIG. 2, a flowchart 200 depicting a method of neural activity control in a subject, is provided in accordance with an embodiment of the present invention. The method includes step of S210 placing a pair of ear pieces of a wearable device on the ears of a subject so that a pair of electrodes placed inside each of the pair of ear pieces contacts the subject's skin wherein each of the pair of electrodes is configured for transmitting electromagnetic field signal of different frequencies to be superimposed at a target region of brain of the subject. In S220 attaching a control module of the wearable device around the neck of the subject wherein the control module is connected to the pair of ear pieces via a pair of coaxial cables for controlling operation of the device; and in S230 driving stimulation between the pair of ear pieces through the superimposed field signals that generate a low frequency refractory wave envelope at the target region wherein the low frequency refractory wave inhibits or stimulates a plurality of local neurons to control electrical neural activity within the target region.

In an embodiment, the superimposition at the target regions is customized where the customization through alteration of angle and orientation of the electrodes is dependent on the target region such as basal ganglia, hippocampus, thalamus, orbitofrontal cortex, anterior cingulate cortex, striatum, prefrontal cortex, hypothalamus, frontal and/or temporal lobes, and amygdala.

In an exemplary embodiment, the device is used to treat Parkinson's disease by targeting the basal ganglia, treat dystonia by targeting the basal ganglia, treat epilepsy by targeting the hippocampus, treat essential tremors by targeting the thalamus, treat obsessive-compulsive disorder by targeting either the orbitofrontal cortex, the anterior cingulate cortex, the striatum, or the thalamus, depending on the affected region, treat chronic pain by targeting the prefrontal cortex, treat cluster headaches by targeting the hypothalamus, treat dementia by targeting the frontal and/or temporal lobes, treat some types of major depressive disorder by targeting the amygdala, thalamus, or hippocampus, treat Huntington's disease by targeting the basal ganglia, treat Tourette's syndrome by targeting the basal ganglia and treat some cases of traumatic brain injury by targeting the frontal and/or temporal lobes. The circularly polarized waves use a corkscrew wave-path that negates the need to line up orientation of waves at contact to achieve maximal superimposition. Further, impedance of electrodes varies depending on the type of treatment and the electrode impedance determines the coaxial cable to match impedance.

Figure 3:
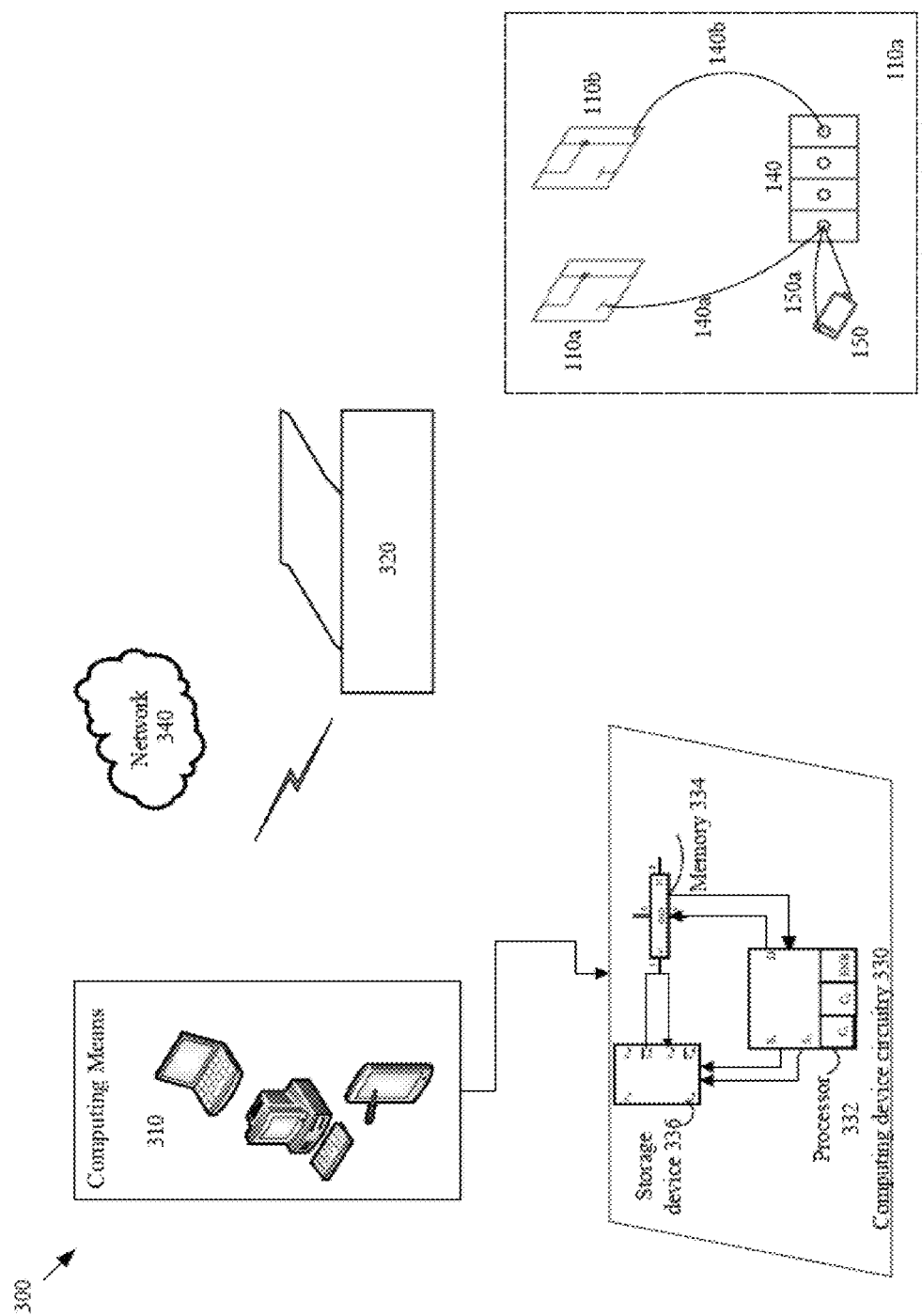
FIG. 3 is a system for manufacturing a wearable device for neural activity control in accordance with an embodiment of the invention.

Referring to FIG. 3 a system 300 for manufacturing a wearable device for neural activity control in a subject is provided in accordance with an embodiment of the present invention. The system 300 includes a computing means 310 configured for analyzing a subject to determine a target region in brain of a subject requiring neural regulation. The computing means 310 analyzes head structure of the subject along with the target region for determining configuration of a pair of ear piece of a wearable device to be manufactured. The system 300 includes a 3D printer 320 configured for receiving a printing command from the computing means 310 to print manufacture the pair of ear piece of the wearable device such that an electrode placed inside each of the pair of ear piece contacts the subject's skin wherein each of the electrodes is configured for transmitting electromagnetic field signals of different frequencies to be superimposed at the target region of brain of the subject to generate a low frequency refractory wave envelope at the target region wherein the low frequency refractory wave inhibits or stimulates a plurality of local neurons to control electrical neural activity within the target region.

In an embodiment, the computing means 310 communicates with the Printer 320 wirelessly through communication interface over a network 340, which may include signal processing circuitry. The computing means 310 includes internal circuitry 330 that may include processor 332, memory 334 and storage device 336 amongst others.

The computing means 310 scans and analyzes cranium of the subject to identify the target region and maps information about the target region with a neurological condition of the subject to determine required angle and orientation of the electrodes for the subject. Also, the target region for neural stimulation to enhance memory, increase productivity and focus of the brain is identified by the computing means.

Figure 4:
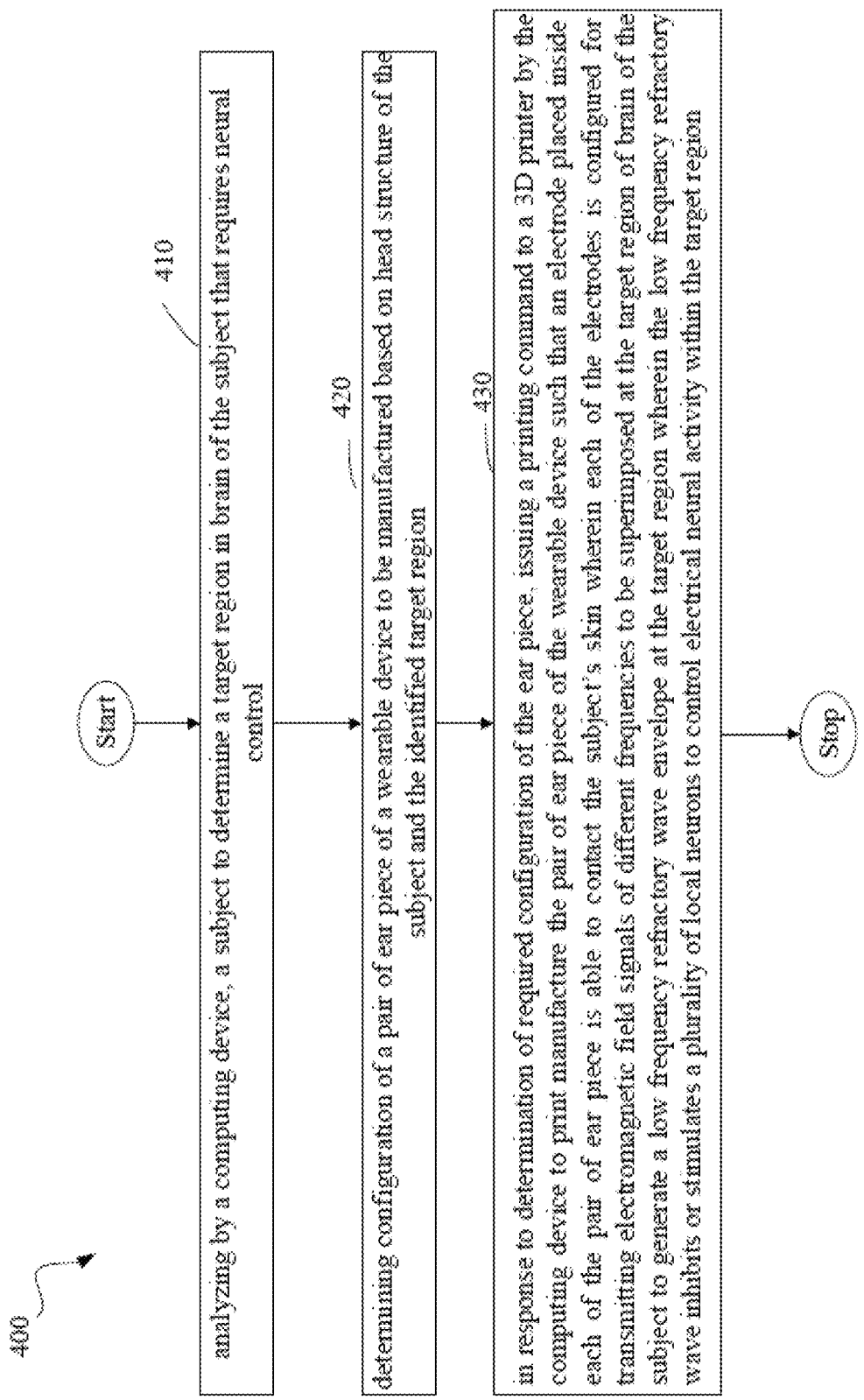
FIG. 4 is a flowchart depicting a method of manufacturing a wearable device for neural activity control in accordance with an embodiment of the invention.

FIG. 4 shows a flowchart 400 depicting a method for manufacturing a wearable device in accordance with an embodiment of the present invention. The method includes the step S410 of analyzing by a computing device, a subject to determine a target region in brain of the subject that requires neural control. In S420 determining configuration of a pair of ear piece of a wearable device to be manufactured based on head structure of the subject and the identified target region; and in S430 in response to determination of required configuration of the ear piece, issuing a printing command to a 3D printer by the computing device to print manufacture the pair of ear piece of the wearable device such that an electrode placed inside each of the pair of ear piece is able to contact the subject's skin wherein each of the electrodes is configured for transmitting electromagnetic field signals of different frequencies to be superimposed at the target region of brain of the subject to generate a low frequency refractory wave envelope at the target region wherein the low frequency refractory wave inhibits or stimulates a plurality of local neurons to control electrical neural activity within the target region.

Since, most neurological disorders are caused by neurons functioning irregularly within certain regions of the brain, when neural activity becomes erratic, human movement, memory, and attitude can be impaired, depending on the affected region of the brain. Irregular neural activity can be treated by use of low electrical frequencies, which can stimulate or inhibit the neurons, depending on the spontaneity of their movement. However, low frequency electromagnetic fields would have to be delivered directly to the affected region, otherwise the fields could influence normally functioning neurons in other regions, thus causing their behavior to become erratic. The device 100 of the present invention sidesteps this issue by delivering two high frequency fields around 2000 khz differing by ~10 khz through the brain. Neurons are unaffected by frequencies in the 2000 kHz range, so these electromagnetic fields travel through normally functioning regions of the brain without issue. The two fields then superimpose at the target region 130 customizable through the angle and orientation of the surface electrodes attached to the apparatus's earpieces. When the fields superimpose, the minute difference between the two frequencies creates a low frequency envelope. This envelope helps regulate erratic neural activity within a highly specified region of the brain without affecting normally functioning regions of the brain.

In an exemplary embodiment, the device 110a is positioned around the ears of the patient by the use of an ear hook-like plastic piece. These earpieces will have the antennas attached to them in order to deliver the high frequency waves. These antennas will then be connected by coaxial cables to a pod that will hang around the patient's neck. The pod will hold the lithium battery, the control module, electromagnetic transmitters (wave generators). The earpieces will be 3D printed from a scan of the patient's ears to make the most effective and comfortable fit on the patient. The filament used will be ABS as it does not absorb electromagnetic radiation.

In an embodiment, the antennas used to deliver the electromagnetic waves are circularly polarized, high pain antennas. High gain antennas help to beam the wave better and create less electrical noise. The circular polarization will help to make the collision the most efficient and consistent compared to traditional sine waves. When two sine waves intersect, they must collide exactly at the nodes to prevent energy loss. However, this issue is sidestepped through the usage of circularly polarized waves as they can intersect at any given portion of the wave without energy loss. This is because circularly polarized waves travel in a corkscrew-like manner created by sine waves traveling in both the x and y directions. Due to the waves alternating in direction, the collision between two circularly polarized waves will always occur at a node.

In an embodiment the antenna used is a circularly polarized patch antenna. The reason for using a patch is to keep the antennas low profile and small enough to fit on the ear hooks. The patch antenna is made from a glass fiber PCB with silver traces in order to allow for the most precise and efficient output of electromagnetic radiation.

In an embodiment, the device 110a utilizes patches with axial ratios close to 0.8 to get the axial ratio of a phased patch antenna. The patch will be phased by using 4 elements to maximize the axial ratio in the price range to stay acceptable. The coaxial cable used to deliver the electromagnetic radiation will be low loss and cut to around a ½ wavelength in order to have the correct phasing for the circularly polarized waves. In order to keep the device as small and light as possible, a lithium battery held in the pod that hangs around the neck will be used. The lithium batteries are housed in a LiPo safe case, during both charging and use in order to ensure the safety of the user.

In an advantageous aspect, the present invention uses TCS—Transcranial Current Stimulation (aka) TES—Transcranial Electrical Stimulation. This variant of transcranial stimulation provides great variability and low safety risk compared to other methods of transcranial stimulation. By implementing TBS, we can use the many forms of electrical stimulation while maintaining a common device to build. The safety aspect of TES is key for the device to be constrained in a small and convenient enough form factor for people to wear daily without the supervision of a physician. The different forms that can be used include but are not limited to TACS—Transcranial Alternating Current Stimulation, TRNS—Transcranial Random Noise Stimulation, and TDCS—Transcranial Direct Current Stimulation. The main principle behind TES is to stimulate and regulate electrical activity with different variations of electrical stimulus through electrodes. The device may use TDCS as the main variant of TES due to its low risk factor compared with the other variants. This is important because the device is targeted towards individuals to administer the treatment by themselves at home. The other methods of TES can also be used to allow the device to better treat a greater extent of conditions caused by irregularity of the electrochemical signals. The device helps people suffering from neurodegenerative disorders and several other hereditary mental illnesses such as non-situational major depression. Due to its ability to personalize the targeted region of the brain, the device is used to treat any neurological condition caused by irregular electrical activity in the brain, and therefore can be utilized by people suffering from any of these conditions, from Parkinson's Disease to dystonia.

The foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that which falls within the scope of the appended claims.

What is claimed is:

1. A wearable device for neural activity control in a subject, the device comprises:
   at least two pairs of electrodes to be placed spaced apart from each other and configured for transmitting electromagnetic field signals of different frequencies to be superimposed at a target region of a brain of a subject;
   a control module connected to the at least two pairs of electrodes for controlling operation of the device, wherein the superimposed field signals generate a low frequency refractory wave envelope at the target region wherein the low frequency refractory wave inhibits or stimulates a plurality of local neurons to control electrical neural activity within the target region in the brain of the subject; and
   a plurality of variable attenuators for controlling magnitude of the refractory waves and circularly polarized waves to minimize energy loss during wave collisions.

2. The device of claim 1 wherein the neural activity includes neural regulation at the target region for treating neurological conditions caused by irregular neural activity in the brain of the subject.

3. The device of claim 1 wherein the neural activity includes neural stimulation at the target region through application of a positive (anodal) or negative (cathodal)

current to the target region, facilitating depolarization or hyperpolarization of neurons wherein the neural stimulation is driven using pulses of direct current to stimulate and enhance memory and cognition.

4. The device of claim 1 further comprises a pair of coaxial cables connecting the control module to the pair of electrodes and a power wire for connecting the control module to a power battery.

5. The device of claim 1 wherein the device provides each of the electrodes as part of an earpiece to be placed around ears of the subject to ensure snug contact between skin of the subject and the electrodes.

6. The device of claim 1 wherein the device includes a circularly polarized patch antenna/electrodes with axial ratio close to 0.8.

7. The device of claim 1 wherein the device includes shielding through copper coating of an inside surface of the control module to maintain electrical integrity to prevent unwanted radiation paths.

8. A wearable device for neural activity control in a subject, the device comprises:
at least two pairs of electrodes to be placed spaced apart from each other and configured for transmitting electromagnetic field signals of different frequencies to be superimposed at a target region of brain of a subject; and
a control module connected to the at least two pairs of electrodes for controlling operation of the device, wherein the superimposed field signals generate a low frequency refractory wave envelope at the target region wherein the low frequency refractory wave inhibits or stimulates a plurality of local neurons to control electrical neural activity within the target region in the brain of the subject wherein the control module is configured to control the at least two pairs of electrodes so that at least one of the at least two pair of electrode generates an electromagnetic field at approximately 2000 khz wherein a difference in frequency between the at least two pair of electrodes is 10 khz.

9. The device of claim 8 wherein the superimposition of the electromagnetic fields at the target region is customizable through an angle and orientation of the at least two pairs of electrodes wherein on superimposition die difference in frequency creates the low frequency envelope that controls the neural activity within the target region of the brain.

10. A method of neural activity control in a subject, the method comprising:
placing a pair of ear pieces of a wearable device on the ears of a subject so that a pair of electrodes placed inside each of the pair of ear pieces contacts the subject's skin wherein each of the pair of electrodes is configured for transmitting electromagnetic field signals of different frequencies to be superimposed at a target region of brain of the subject;
attaching a control module of the wearable device around the neck of the subject wherein the control module is connected to the pair of ear pieces via a pair of coaxial cables for controlling operation of the device; and
driving stimulation between the pair of ear pieces through the superimposed field signals that generate a low frequency refractory wave envelope at the target region wherein the low frequency refractory wave inhibits or stimulates a plurality of local neurons to control electrical neural activity within the target region.

11. The method of claim 10 further comprising customization of the superimposition of the electromagnetic fields at the target region through an angle and orientation of the pair of electrodes wherein on superimposition the difference in frequency creates the low frequency envelope that control neural activity by neural regulation or neural stimulation within the target region of the brain.

12. The method of claim 11 wherein the customization through alteration of angle and orientation of the pair of electrodes is dependent on the target region such as basal ganglia, hippocampus, thalamus, orbitofrontal cortex, anterior cingulate cortex, striatum, prefrontal cortex, hypothalamus, frontal and/or temporal lobes, and amygdala.

\* \* \* \* \*